(12) United States Patent
Alanine et al.

(10) Patent No.: US 6,730,670 B2
(45) Date of Patent: May 4, 2004

(54) 7-PHENYL-BENZO[B]THIOPHEN AMIDE DERIVATIVES

(75) Inventors: Alexander Alanine, Schlierbach (FR); Alexander Flohr, Basle (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/315,821

(22) Filed: Dec. 10, 2002

(65) Prior Publication Data

US 2003/0149030 A1 Aug. 7, 2003

(30) Foreign Application Priority Data

Dec. 12, 2001 (EP) .............................................. 01129269

(51) Int. Cl.⁷ .................... C07D 417/12; C07D 413/12; C07D 333/12; A61K 31/5377; A61P 25/16
(52) U.S. Cl. ................. 514/228.2; 514/233.5; 514/252.13; 514/324; 514/443; 544/62; 544/145; 544/376; 546/202; 549/51
(58) Field of Search ............................ 514/228.2, 233.5, 514/252.13, 324, 443; 544/62, 145, 376; 546/202; 549/51

(56) References Cited

U.S. PATENT DOCUMENTS

| | | | | | |
|---|---|---|---|---|---|
| 5,350,748 A | * | 9/1994 | Boschelli et al. | ......... | 514/237.2 |
| 6,514,989 B1 | * | 2/2003 | Nettekoven et al. | ......... | 514/303 |
| 6,521,754 B2 | * | 2/2003 | Alanine et al. | ............. | 544/129 |
| 6,545,000 B1 | * | 4/2003 | Shimada et al. | ....... | 514/259.31 |

FOREIGN PATENT DOCUMENTS

| | | |
|---|---|---|
| EP | 568289 | 11/1993 |
| EP | 0 915 087 | 5/1999 |
| WO | WO 99 21617 | 5/1999 |

OTHER PUBLICATIONS

DeNinno, M.P., Annual Reports in Medicinal Chemistry, 33, 1998, 111–120.*
Poulsen et al., Bioorganic & Med. Chem., vol. 6, pp. 619–641 (1998).
Muller et al., Bioorganic & Med. Chem., vol. 6, pp. 707–719 (1998).
Kim et al., J. Med. Chem., vol. 41, pp. 2835–2845 (1998).
Li et al., J. Med. Chem., vol. 41, pp. 3186–3201 (1998).
Baraldi et al., J. Med. Chem., vol. 41, pp. 2126–2133 (1998).
Li et al., J. Med. Chem., vol. 42, pp. 706–721 (1999).
Baraldi et al., J. Med. Chem., vol. 39, pp. 1164–1171 (1996).
Colotta et al., Arch. Pharm. Med. Chem., vol. 332, pp. 39–41 (1999).
Domoki et al., Am. J. Physiol., vol. 276, pp. H1113–H1116 (1999).
Haas et al., Naunyn Schmeiedeberg's Arch. Pharmacol., vol. 362, pp. 375–381 (2000).
A.J. Bridges et al., Tetrahedron Letters, vol. 33(49), pp. 7499–7502 (1992).

\* cited by examiner

Primary Examiner—Mukund J. Shah
Assistant Examiner—Thomas McKenzie
(74) Attorney, Agent, or Firm—George W. Johnston; Patricia S. Rocha-Tramaloni; Kimberly J. Prior

(57) ABSTRACT

A compound of the formula

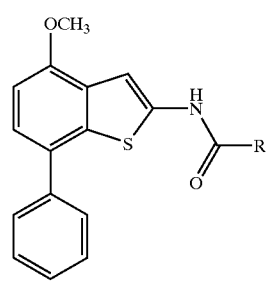

I

Compounds of formula I have a good affinity to the A2A receptor and are useful for the treatment of diseases mediated by this receptor.

16 Claims, No Drawings

7-PHENYL-BENZO[B]THIOPHEN AMIDE DERIVATIVES

FIELD OF INVENTION

The present invention is directed to a compound of the formula

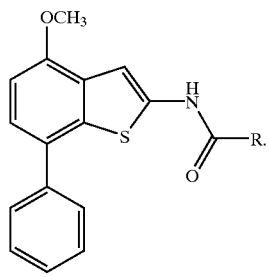

I

Compounds of formula I are adenosine receptor ligands. Specifically, the compounds of the present invention have a good affinity to the $A_{2A}$-receptor and a high selectivity to the $A_1$- and $A_3$ receptors and as such, are useful in a method of treatment, control or prevention of illnesses based on the modulation of the adenosine system.

BACKGROUND

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzyme A; and to RNA. Together adenosine and these related compounds are important in the regulation of many aspects of cellular metabolism and in the modulation of different central nervous system activities.

The receptors for adenosine have been classified as $A_1$, $A_{2A}$, $A_{2B}$ and $A_3$ receptors, belonging to the family of C protein-coupled receptors. Activation of adenosine receptors by adenosine initiates signal transduction mechanism. These mechanisms are dependent on the receptor associated G protein. Each of the adenosine receptor subtypes has been classically characterized by the adenylate cyclase effector system, which utilizes cAMP as a second messenger. The $A_1$ and $A_3$ receptors, coupled with $G_i$ proteins inhibit adenylate cyclase, leading to a decrease in cellular CAMP levels, while $A_{2A}$ and $A_{2B}$ receptors couple to $G_s$ proteins and activate adenylate cyclase, leading to an increase in cellular CAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326–328 amino acids) was cloned from various species (canine, human, rat, dog, chick, bovine, guinea-pig) with 90–95% sequence identify among the mammalian species. The $A_{2A}$ receptor (409–412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317–320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The actions of both subtypes is to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is a neuromodulator, able to modulate many aspects of physiological brain function. Endogenous adenosine, a central link between energy metabolism and neuronal activity, varies according to behavioral state and (patho) physiological conditions. Under conditions of increased demand and decreased availability of energy (such as hypoxia, hypoglycemia, and/or excessive neuronal activity), adenosine provides a powerful protective feedback mechanism. Interacting with adenosine receptors represents a promising target for therapeutic intervention in a number of neurological and psychiatric diseases such as epilepsy, sleep, movement disorders (Parkinson or Huntington's disease), Alzheimer's disease, depression, schizophrenia, or addiction. An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore maybe used as antiepileptic agents. Adenosine antagonists stimulate the activity of the CNS and have proven to be effective as cognition enhancers.

Selective $A_{2a}$ antagonists have therapeutic potential in the treatment of various forms of dementia, for example in Alzheimer's disease, and of neurodegenerative disorders, e.g. stroke. Adenosine $A_{2a}$ receptor antagonists modulate the activity of striatal GABAergic neurons and regulate smooth and well-coordinated movements, thus offering a potential therapy for Parkinsonian symptoms. Adenosine is also implicated in a number of physiological processes involved in sedation, hypnosis, schizophrenia, anxiety, pain, respiration, depression, and drug addiction (amphetamine, cocaine, opioids, ethanol, nicotine, cannabinoids). Drugs acting at adenosine receptors therefore have therapeutic potential as sedatives, muscle relaxants, antipsychotics, anxiolytics, analgesics, respiratory stimulants, antidepressants, and to treat drug abuse. They may also be used in the treatment of ADHD (attention deficit hyperactivity disorder).

An important role for adenosine in the cardiovascular system is as a cardioprotective agent. Levels of endogenous adenosine increase in response to ischaemia and hypoxia, and protect cardiac tissue during and after trauma (preconditioning). By acting at the $A_1$ receptor, adenosine $A_1$ agonists may protect against the injury caused by myocardial ischemia and reperfusion. The modulating influence of $A_2a$ receptors on adrenergic function may have implications for a variety of disorders such as coronary artery disease and heart failure. $A_{2a}$ antagonists may be of therapeutic benefit in situations in which an enhanced antiadrenergic response is desirable, such as during acute myocardial ischemia. Selective antagonists at $A_{2a}$ receptors may also enhance the effectiveness of adenosine in terminating supraventricular arrhytmias.

Adenosine modulates many aspects of renal function, including renin release, glomerular filtration rate and renal blood flow. Compounds which antagonise the renal affects of adenosine have potential as renal protective agents. Furthermore, adenosine $A_3$ and/or $A_{2B}$ antagonists may be useful in the treatment of asthma and other allergic responses or and in the treament of diabetes mellitus and obesity.

The current knowledge on adenosine receptors is summarized in various documents including, for example the following publications:

Bioorganic & Medicinal Chemistry, 6, (1998), 619–641,
Bioorganic & Medicinal Chemistry, 6, (1998), 707–719,
J. Med. Chem., (1998), 41, 2835–2845,
J. Med. Chem., (1998), 41, 3186–3201,
J. Med. Chem., (1998), 41, 2126–2133,
J. Med. Chem., (1999), 42, 706–721,
J. Med. Chem., (1996), 39, 1164–1171,
Arch. Pharm. Med. Chem., 332, 39–41, (1999),
Am. J. Physiol., 276, H113–1116, (1999) or
Naunyn Schmied, Arch. Pharmacol. 362, 375–381, (2000).

SUMMARY

The present invention is directed to a compound of the formula

I

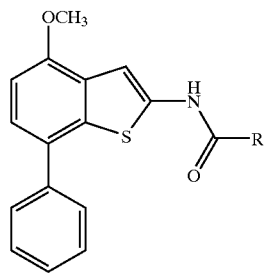

wherein
R is selected from the group phenyl, phenyl substituted by halogen, pyridin 3-or 4-yl, pyridin 3- or 4-yl substituted by lower alkyl, and —$NR^1R^2$, wherein $R^1$ and $R^2$, together with the N atom to which they are attached, form heterocyclic rings, selected from the group consisting of morpholinyl, thiomorpholinyl, piperidinyl and piperazinyl, said heterocyclic rings being unsubstituted or substituted by —$(CH_2)_n$-hydroxy, lower alkyl or lower alkoxy; and
n is 0, 1 or 2;
or a pharmaceutically acceptable acid addition salt thereof.

It has surprisingly been found that the compounds of formula I are adenosine receptor ligands. Specifically, the compounds of the present invention have a good affinity to the $A_{2A}$-receptor and a high selectivity to the $A_1$- and $A_3$ receptors.

The present invention is directed to a compound of formula I, or a pharmaceutically acceptable salt thereof, as well as processes for the preparation of compounds of formula 1. The present invention is also directed to a pharmaceutical composition comprising a therapeutically effective amount of a compound of formula I, or a pharmaceutically acceptable salt, thereof in a pharmaceutically acceptable carrier for the treatment of diseases, related to the adenosine $A_2$ receptor. The present invention also is directed to a method of control or prevention of illnesses based on the modulation of the adenosine system, such as Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, cannabinoids, or against asthma, allergic responses, hypoxia, ischaemia, seizure and substance abuse. Furthermore, compounds of the present invention maybe useful as sedatives, muscle relaxants, antipsychotics, antiepileptics, anticonvulsants and cardiaprotective agents for disorders such as coronary artery disease and heart failure comprising administering a therapeutically effective amount of a compound-of formula I or a pharmaceutically acceptable salt thereof to a person in need of such treatment. The most preferred indications in accordance with the method of control or treatment of the present invention are those, which depend on $A_{2A}$ receptor antagonistic activity and which include disorders of the central nervous system, for example the treatment or prevention of Alzheimer's disease, certain depressive disorders, drug addiction, neuroprotection and Parkinson's disease as well as ADHD.

DETAILED DESCRIPTION

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "halogen" denotes chlorine, iodine, fluorine and bromine.

The term "lower alkoxy" denotes a group wherein the alkyl residue is as defined above, and which is attached via an oxygen atom.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Preferred compounds of the present application are compounds of formula I, wherein R is thiomorpholinyl, for example the following compound:
thiomorpholine-4-carboxylic acid (4-methoxy-7-phenyl-benzo[b]thiophen-2-yl)-amide.

Further preferred are compounds of formula 1, wherein R is morpholinyl, for example the following compound:
morpholine-4-carboxylic acid (4-methoxy-7-phenyl-benzo[b]thiophen-2-yl)-amide.

Further preferred are compounds, wherein R is piperidinyl, optionally substituted by hydroxy, methoxy or —$CH_2OH$, for example the following compounds:
piperidine-1-carboxylic acid (4-methoxy-7-phenyl-benzo[b]thiophen-2-yl)-amide,
4-hydroxy-piperidine-1-carboxylic acid (4-methoxy-7-phenyl-benzo[b]thiophen-2-yl)-amide,
4-methoxy-piperidine-1-carboxylic acid (4-methoxy-7-phenyl-benzo[b]thiophen-2-yl)-amide or
4-hydroxymethyl-piperidine-1-carboxylic acid (4-methoxy-7-phenyl-benzo[b]thiophen-2-yl)-amide.

Further preferred are compounds, wherein R is piperazinyl, substituted by methyl, for example the following compound:
4-methyl-piperazine-1-carboxylic acid (4-methoxy-7-phenyl-benzo[b]thiophen-2-yl)-amide.

A preferred group of compounds is further those, wherein R is phenyl, optionally substituted by halogen, or is pyridin 3-or 4-yl, optionally substituted by lower alkyl, for example the following compounds:

N-(4-methoxy-7-phenyl-benzo[b]thiophen-2-yl)-6-methyl-nicotinamide,
N-(4-methoxy-7-phenyl-benzo[b]thiophen-2-yl)-2-methyl-isonicotinamide or
4-fluoro-N-(4-methoxy-7-phenyl-benzo[b]thiophen-2-yl)-benzamide.

The present compounds of formula I and their pharmaceutically acceptable salts can be prepared by methods known in the art, for example, by processes described below, which processes comprise
reacting a compound of formula

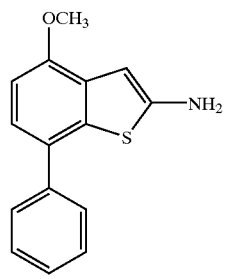

(2)

with a compound of formula

RC(O)Cl    (3)

forming a compound of formula

IA

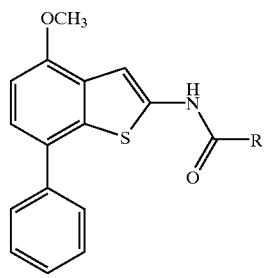

wherein R is phenyl, optionally substituted by halogen, or is pyridin 3-or 4-yl, optionally substituted by lower alkyl, or reacting a compound of formula

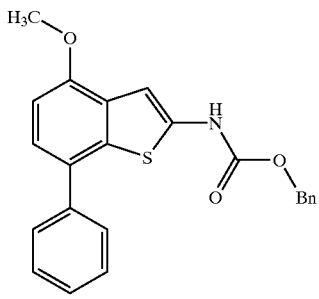

(5)

with a compound of formula $HNR^1R^2$
forming a compound of formula

IB

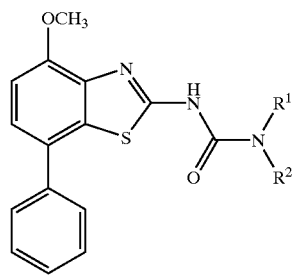

wherein $R^1$ and $R^2$, together with the N atom to which they are attached, form heterocyclic rings, selected from the group consisting of morpholinyl, thiomorpholinyl, piperidinyl or piperazinyl, optionally substituted by —$(CH_2)_n$-hydroxy, lower alkyl or lower alkoxy, and if desired, converting the compounds obtained into pharmaceutically acceptable acid addition salts.

The compounds of formula I may be prepared in accordance with process variants a) and b) and with the following scheme 1.10 Examples are further described in more detail.

Scheme 1

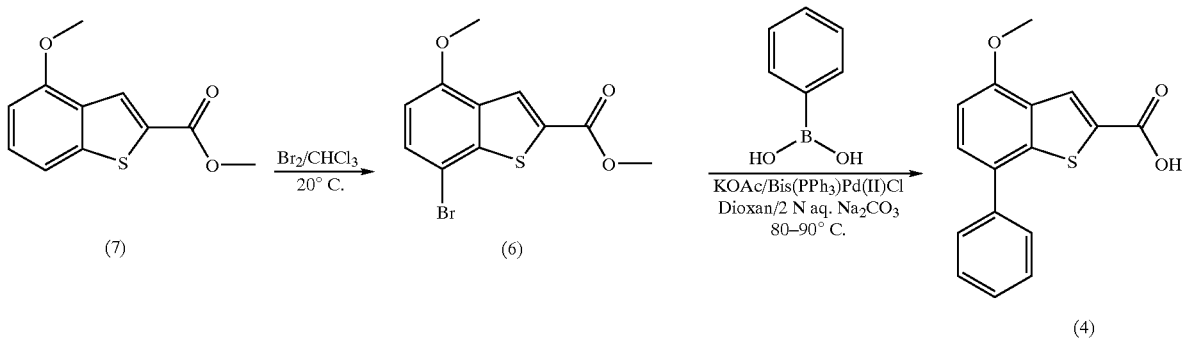

a) SOCl2, reflux
b) NaN3, acetone, 0° C.
c) BnOH/1,2-DCE, 80° C.

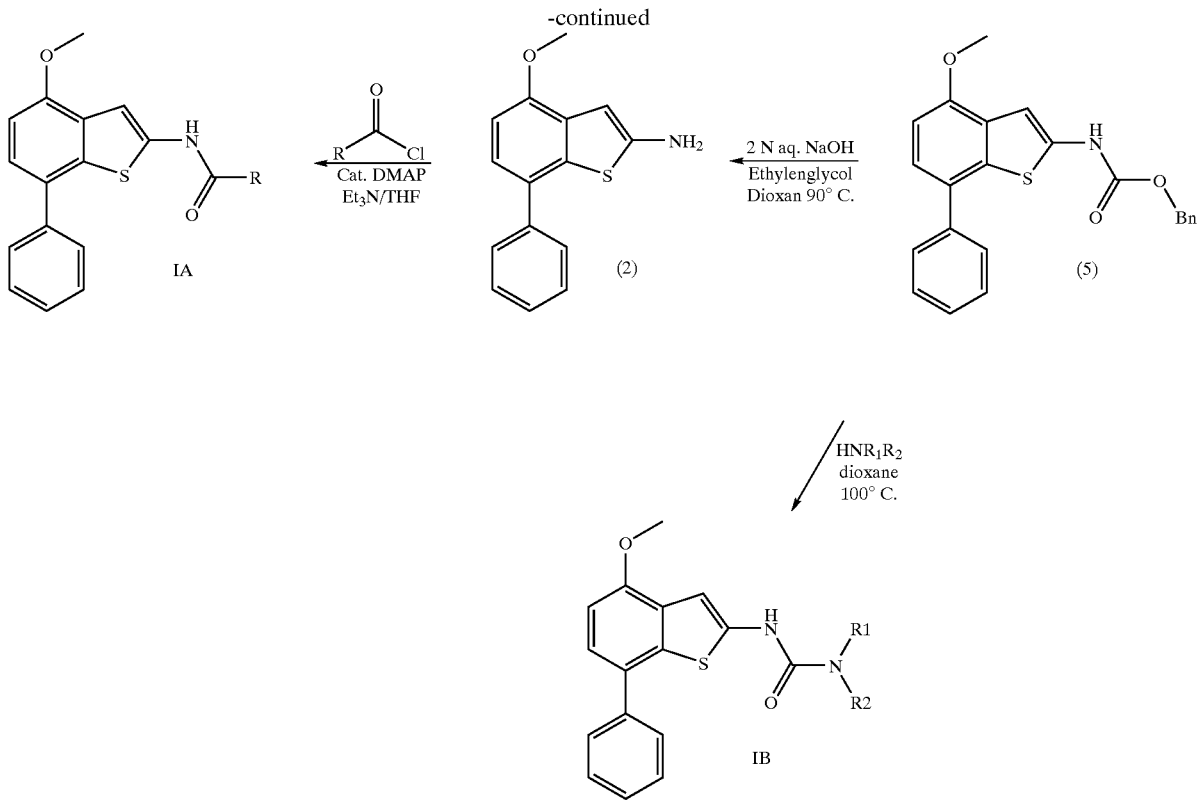

R, R[1] and R[2] are as defined above and
DPPA is diphenylphosphoryl azide,
DMF is dimethylformamide and
DMAP is 4-dimethylaminopyridine.
O—Bn is a benzyl ester.

In accordance with scheme 1, the compounds of formula IA and IB are prepared as follows:

4-Methoxy-benzo[b]thiophene-2-carboxylic acid methyl ester (7) is prepared in two steps from 3-fluoroanisidine according to the following literature:

*Tetrahedron Lett.* (1992), 33(49), 7499–7502.

7-Bromo-4-methoxy-benzo[b]thiophene-2-carboxylic acid methyl ester (6) is prepared according to the literature (*Eur. Pat. Appl.* (1993), 72 pp. EP 568289, CAN 120:298461) by treatment of 4-methoxy-benzo[b]thiophene-2-carboxylic acid methyl ester with bromine in chloroform at 0° C. to 20° C.

The compound of formula (4), 4-methoxy-7-phenyl-benzo[b]thiophene-2-carboxylic acid is prepared as follows: a suspension of 7-bromo-4-methoxy-benzo[b]thiophene-2-carboxylic acid methyl ester (6), bis(triphenylphosphine)palladium (II) chloride and $K_2CO_3$ under argon in dioxane at 20° C. is stirred for about 60 minutes. Phenylboronic acid and $Na_2CO_3$ is then added and the mixture is heated to about 100° C. overnight. After cooling, filtration and acidification to pH I with hydrochloric acid the product of formula (4) is precipitated and is filtered off and dried under vacuum.

Further, under an argon atmosphere at 20° C. is added 4-methoxy-7-phenyl-benzo[b]thiophene-2-carboxylic acid (4) portion wise to a stirred solution of thionylchloride. The reaction is heated for 1 h under reflux then cooled and evaporated to dryness. The crude residue was then suspended in a small volume of acetone and sodium azide is added at 0° C. and stirred for 1 h. Following this the reaction was poured onto ice, extracted twice with ether and dried with MgSO4, filtered and the solvent evaporated. The acyl azide was then taken up in 1,2-dichloro ethane and benzyl alcohol is added and the mixture is heated to 85° C. overnight. After cooling the reaction mixture is evaporated to dryness and purified by flash chromatography over silica gel. This afforded the pure (4-methoxy-7-phenyl-benzo[b]thiophen-2-yl)-carbamic acid benzyl ester (5).

The compound of formula (2), (4-methoxy-7-phenyl-benzo[b]thiophen-2-yl)-amine, is prepared as described below:

A stirred solution of (4-methoxy-7-phenyl-benzo[b]thiophen-2-yl)-carbamic acid benzyl ester (5) in ethylene gylcol and dioxane is heated under reflux with NaOH for about 4 h. After cooling and addition of water the mixture is extracted with EtOAc, the combined extracts are washed with brine, dried with $Na_2SO_4$ filtered and evaporated. The crude residue is then chromatographed over silica gel.

Preparation of a Compound of Formula IA

A solution of (4-methoxy-7-phenyl-benzo[b]thiophen-2-yl)-amine (2) in THF and diethylisopropyl amine is stirred together at about −10° C. under an argon atmosphere. To this is slowly added a compound of formula RC(O)Cl, wherein R is phenyl, optionally substituted by halogen, or is pyridin 3-or 4-yl, optionally substituted by lower alkyl, in dichloromethane and the mixture is stirred to 20° C. overnight. The reaction is again cooled to 0° C. and methanol is then added and the mixture is stirred for 30 min to 20° C. The mixture is then evaporated to dryness and chromatographed over silica gel.

Preparation of a Compound of Formula IB

In accordance with scheme 1, a compound of formula IB is prepared by the following way:

A stirred solution of (4-methoxy-7-phenyl-benzo[b]thiophen-2-yl)-carbamic acid benzyl ester (5) in dioxane is heated with a compound of formula $HNR^1R^2$, wherein $R^1$ and $R^2$ form together with the N atom to which they are attach heterocyclic rings, selected from the group consisting of morpholinyl, thiomorpholinyl, piperidinyl or piperazinyl, optionally substituted by —$(CH_2)_n$- hydroxy, lower alkyl or lower alkoxy for about 68 h at reflux under argon. After cooling the reaction the solvents are evaporated and the residue is chromatographed over silica gel. The product fractions are then combined, evaporated and dried under vacuum. A compound of formula IB is obtained.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Preparations and Examples herein below. However, other equivalent separation or isolation procedures could, of course, also be used.

Salts of Compounds of Formula I

The compounds of formula I may be basic, for example in cases where the residue R contains a basic group such as an aliphatic or aromatic amine moiety. In such cases the compounds of Formula I may be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention are adenosine receptor ligands and possess a high affinity towards the adenosine $A_{2A}$ receptor and a good selectivity towards $A_1$ and $A_3$ receptors.

The compounds were investigated in accordance with the following test.

Human Adenosine $A_{2A}$ Receptor

The human adenosine $A_{2A}$ receptor was recombinantly expressed in chinese hamster ovary (CHO) cells using the semliki forest virus expression system. Cells were harvested, washed twice by centrifugation, homogenized and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^3$H]-SCH-58261 (Dionisotti et al., 1997, Br J Pharmacol 121, 353; 1 nM) binding assay was carried out in 96-well plates in the presence of 2.5 µg of membrane protein, 0.5 mg of Ysi-poly-1-lysine SPA beads and 0.1 U adenosine deaminase in a final volume of 200 µl of buffer A. Non-specific binding was defined using xanthine amine congener (XAC; 2 µM). Compounds were tested at 10 concentrations from 10 µM-0.3 nM. All assays were conducted in duplicate and repeated at least two times. Assay plates were incubated for 1 hour at room temperature before centricentrifugation and then bound ligand determined of test compound using a Packard Topcount scintillation counter. $IC_{50}$ values, the concentration where 50% of the non-specific binding is displaced, were calculated using a non-linear curve fitting program and Ki values calculated using the Cheng-Prussoff equation.

Desirable affinity to the $A_{2A}$ receptor is shown in the table below. Preferred compounds of formula I have a pKi>6.4.

| Example No. | $hA_2$ (pKi) |
|---|---|
| 1 | 6.81 |
| 2 | 6.58 |
| 3 | 6.59 |
| 4 | 6.90 |
| 5 | 6.46 |
| 6 | 7.01 |
| 7 | 6.62 |
| 8 | 6.52 |
| 9 | 6.41 |
| 10 | 7.36 |

The compounds of formula I and the pharmaceutically acceptable salts of the compounds of formula I can be used to prepare pharmaceutical compositions. The pharmaceutical compositions can be administered orally, e.g. in the form of tablets, coated tablets, dragees, hard and soft gelatine capsules, solutions, emulsions or suspensions. The administration can, however, also be effected rectally, e.g. in the form of suppositories, parenterally, e.g. in the form of injection solutions.

The compounds of formula I can be processed with pharmaceutically inert, inorganic or organic carriers for the production of pharmaceutical compositions. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As stated above, the present invention is directed to pharmaceutical compositions containing a compound of formula I or a pharmaceutically acceptable salt thereof and a therapeutically inert carrier, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention a method of treatment, control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse comprises administering a therapeutically effective amount of a compound of formula I or a pharmaceutically acceptable salt thereof to a person in need of such treatment. Further, compounds of the present invention maybe useful as sedatives, muscle relaxants, antipsychotics, antiepileptics, anticonvulsants and cardioprotective agents and for the production of corresponding pharmaceutical compositions.

The most preferred indications in accordance with method of treatment of the present invention include disorders of the central nervous system, for example the treatment or prevention of certain depressive disorders, neuroprotection and Parkinson's disease.

The dosage can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage may be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The following preparation and examples illustrate the invention but are not intended to limit its scope.

EXAMPLE 1

Thiomorpholine-4-carboxylic acid (4-methoxy-7-phenyl-benzo[b]thiophen-2-yl)-amide A stirred solution of (4-methoxy-7-phenyl-benzo[b]thiophen-2-yl)-carbamic acid benzyl ester (200 mg, 0.513 mmol) in dioxane (5 ml) was heated with thiomorpholine (10 eq., 5.13 mmol) for 68 h at reflux under argon. After cooling the reaction the solvents were evaporated and the residue was chromatographed over silica gel eluting with heptane/EtOAc (1:2). The product fractions were then combined, evaporated and dried under vacuum at 60° C. to afford the pure title product (94 mg, 47% yield) as a light brown solid MS m/e=383.2 (M−H).

EXAMPLE 2

Morpholine-4-carboxylic acid (4-methoxy-7-phenyl-benzo[b]thiophen-2-yl)-amide

The title compound MS: mi/e=369.3 (M+H$^+$) was obtained as a light brown solid (58% yield) by the reaction of morpholine with (4-methoxy-7-phenyl-benzo[b]thiophen-2-yl)-carbamic acid benzyl ester according to the method described above for example 1.

EXAMPLE 3

Piperidine-1-carboxylic acid (4-methoxy-7-phenyl-benzo[b]thiophen-2-yl)-amide

The title compound MS: m/e=365.1 (M−H) was obtained as a light brown solid (62% yield) by the reaction of piperidine with (4-methoxy-7-phenyl-benzo[b]thiophen-2-yl)-carbamic acid benzyl ester according to the method described above for example 1.

EXAMPLE 4

4-Hydroxy-piperidine-1-carboxylic acid (4-methoxy-7-phenyl-benzo[b]thiophen-2-yl)-amide The title compound MS: m/e=381.2 (M−H) was obtained as a light brown solid (54% yield) by the reaction of 4-hydroxy-piperidine with (4-methoxy-7-phenyl-benzo[b]thiophen-2-yl)-carbamic acid benzyl ester according to the method described above for example 1.

EXAMPLE 5
4-Methoxy-piperidine-1-carboxylic acid (4-methoxy-7-phenyl-benzo[b]thiophen-2-yl)-amide The title compound MS: m/e 395.3 (M−H) was obtained as a light brown solid (54% yield) by the reaction of 4-methoxy-piperidine with (4-methoxy-7-phenyl-benzo[b]thiophen-2-yl)-carbamic acid benzyl ester according to the method described above for example 1.

EXAMPLE 6
4-Hydroxymethyl-piperidine-1-carboxylic acid (4-methoxy-7-phenyl-benzo[b]thiophen-2-yl)-amide The title compound MS: m/e=395.2 (M−H) was obtained as a light yellow solid (53% yield) by the reaction of 4-piperidine-methylalcohol with (4-methoxy-7-phenyl-benzo[b]thiophen-2-yl)-carbamic acid benzyl ester according to the method described above for example 1.

EXAMPLE 7
4-Methyl-piperazine-1-carboxylic acid (4-methoxy-7-phenyl-benzo[b]thiophen-2-yl)-amide The title compound MS: m/e=380.2 (M−H) was obtained as a light yellow foam (46% yield) by the reaction of N-methyl-piperizine with (4-methoxy-7-phenyl-benzo[b]thiophen-2-yl)-carbamic acid benzyl ester according to the method described above for example 1.

EXAMPLE 8
N-(4-Methoxy-7-phenyl-benzo[b]thiophen-2-yl)-6-methyl-nicotinamide A solution of (4-methoxy-7-phenyl-benzo[b]thiophen-2-yl)-amine (100 mg, 0.392 mmol) in THF (8 ml) and diethylisopropyl amine (0.147 ml, 2.2 eq.) was stirred together at −10° C. under an argon atmosphere. To this was slowly added 6-methyl-nicotinyl chloride hydrochloride (83 mg, 0.431 mmol, 1.1 eq) in dichloromethane (5 ml) and the mixture stirred to 20° C. overnight. The reaction was again cooled to 0° C. and Methanol was then added (1.2 ml) and the mixture stirred for 30 min to 20° C. The mixture was then evaporated to dryness and chromatographed over silica gel eluting with a gradient of heptane/EtOAc (1:1 to 1:8). The product fractions were pooled and evaporated to afford the title compound (83 mg, 57% yield) as a yellow solid MS: m/e=375.4 (M+H$^+$).

EXAMPLE 9
N-(4-Methoxy-7-phenyl-benzo[b]thiophen-2-yl)-2-methyl-isonicotinamide The title compound MS: m/e=375.4 (M+H$^+$) was obtained as a light yellow solid (27% yield) by the reaction of 2-methyl-isonicotinyl chloride hydrochloride with (4-methoxy-7-phenyl-benzo[b]thiophen-2-yl)-amine according to the method described above for example 8.

EXAMPLE 10
4-Fluoro-N-(4-methoxy-7-phenyl-benzo[b]thiophen-2-yl)-benzamide

A solution of (4-methoxy-7-phenyl-benzo[b]thiophen-2-yl)-amine (100 mg, 392 mmol) in THF (5 ml) with triethylamine (0.049 ml, 0.9 eq.) and DMAP (5 mg, 0.1 eq) was stirred together at 0° C. under an argon atmosphere. To this was slowly added 4-fluorobenzoyl chloride (0.038 ml, 314 mmol, 0.8 eq.) and the mixture stirred to 20° C. over 2 h. The mixture was then evaporated to dryness and chromatographed over silica gel eluting with a gradient of heptane/EtOAc (6:1 to 2:1). The product fractions were pooled and evaporated to afford the title compound (74 mg, 50% yield) as a yellow solid MS: m/e=378.3 (M+H$^+$).

Intermediates

EXAMPLE 11
(4-Methoxy-7-phenyl-benzo[b]thiophen-2-yl)-amine

A stirred solution of (4-methoxy-7-phenyl-benzo[b]thiophen-2-yl)-carbamic acid benzyl ester (1.7 g, 4.36 mmol) in ethylene gylcol and dioxane was heated under reflux with 2N NaOH (20 ml, 9.1 eq) for 4 h. After cooling and addition of water (20 ml) the mixture was extracted with EtOAc (3×25 ml), the combined extracts were washed with brine, dried with Na$_2$SO$_4$ filtered and evaporated. The crude residue was then chromatographed over silica gel eluting with dichloromethane/2N NH$_3$ in MeOH (99:1). This afforded the title compound (668 mg, 60% yield) as a red gum. MS m/e=256.2 (M$^+$)

EXAMPLE 12
(4-Methoxy-7-phenyl-benzo[b]thiophen 2-yl)-carbamic acid benzyl ester Under an argon atmosphere at 20° C. was added 4-methoxy-7-phenyl-benzo[b]thiophene-2-carboxylic acid (300 mg, 1.06 mmol) portion wise to a stirred solution of thionylchloride (1.3 ml). The reaction was heated for 1 h under reflux then cooled and evaporated to dryness. The crude residue was then suspended in a small volume of acetone and sodium azide (75 mg, 1.15 mmol, 1.1 eq.) added at 0° C. and stirred for 1 h. Following this the reaction was poured onto ice, extracted twice with ether and dried with MgSO4, filtered and the solvent evaporated. The acyl azide was then taken up in 1,2-dichloro ethane and benzyl alcohol added and the mixture heated to 85° C. overnight. After cooling the reaction mixture was evaporated to dryness and purified by flash chromatography over silica gel eluting with dichloromethane/heptane (3:1). This afforded the pure title compound (332 mg, 81% yield) as a yellow oil. MS m/e= 390.3 (M+H$^+$)

EXAMPLE 13
4-Methoxy-7-phenyl-benzo[b]thiophene-2-carboxylic acid

A suspension of 7-bromo-4-methoxy-benzo[b]thiophene-2-carboxylic acid methyl ester (5 g, 16.6 mmol) with bis(triphenylphosphine)palladium (II) chloride (350 mg, 0.496 mmol, 0.03 eq.) and K$_2$CO$_3$ (4.88 g, 49.8 mmol, 3 eq.) under argon in dioxane (40 ml) at 20° C. was stirred for 60 minutes. Phenylboronic acid (2.16 g, 17.4 mmol, 1.05 eq.) and 2N Na$_2$CO$_3$ (80 ml) was then added and the mixture heated to 100° C. overnight. After cooling, filtration and acidification to pH 1 with aq. HCl the product precipitated and was filtered off and dried under vacuum at 50° C. to afford the title compound (3.16 g, 67% yield) as a light brown solid. MS m/z=282.9 (M−H).

EXAMPLE 14
7-Bromo-4-methoxy-benzo[b]thiophene-2-carboxylic acid methyl ester The title compound was prepared as an off-white solid (m.p. 112° C.) according to the literature by treatment of 4-methoxy-benzo[b]thiophene-2-carboxylic acid methyl ester with bromine in chloroform at 0° C. to 20° C.

Reference: Bridges, Alexander; Schwartz, C. Eric; Littlefield, Bruce A. Eur. Pat. Appl. (1993), 72 pp. EP 568289, CAN 120:298461.

EXAMPLE 15

4-Methoxy-benzo[b]thiophene-2-carboxylic acid methyl ester

The title compound was prepared in two steps from 3-fluoroanisidine as an off-white solid (m.p. 74° C.) according to according the literature.

Reference: Bridges, Alexander J.; Lee, Arthur; Maduakor, Emmanuel C.; Schwartz, C. Eric.;
*Tetrahedron Lett.* (1992), 33(49), 7499–7502.

What is claimed is:

1. A compound of the formula

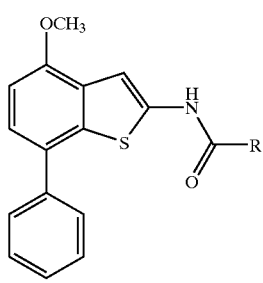

I wherein
  R is selected from the group phenyl, phenyl substituted by halogen, pyridin 3-or 4-yl, pyridin 3- or 4-yl substituted by lower alkyl and —$NR^1R^2$, wherein $R^1$ and $R^2$, together with the N atom to which they are attached, form heterocyclic rings, selected from the group consisting of
    morpholinyl, thiomorpholinyl, piperidinyl and piperazinyl, said heterocyclic rings being unsubstituted or substituted by —$(CH_2)_n$-hydroxy, lower alkyl or lower alkoxy; and
  n is 0, 1 or 2;
  or a pharmaceutically acceptable acid addition salt thereof.

2. (Original) The compound of formula I in accordance with claim 1, wherein R is thiomorpholinyl.

3. The compound of formula I in accordance with claim 2, wherein the compound is thiomorpholine-4-carboxylic acid (4-methoxy-7-phenyl-benzo[b]thiophen-2-yl)-amide.

4. The compound of formula I in accordance with claim 1, wherein R is morpholinyl.

5. The compound of formula I in accordance with claim 4, wherein the compound is morpholine-4-carboxylic acid (4-methoxy-7-phenyl-benzo[b]thiophen-2-yl)-amide.

6. The compound of formula I in accordance with claim 1, wherein R is piperidinyl or piperidinyl substituted by hydroxy, methoxy or —$CH_2OH$.

7. The compound of formula I in accordance with claim 6, wherein the compound is selected from the group consisting of piperidine-1-carboxylic acid (4-methoxy-7-phenyl-benzo[b]thiophen-2-yl)-amide, 4-hydroxy-piperidine-1-carboxylic acid (4-methoxy-7-phenyl-benzo[b]thiophen-2-yl)-amide, 4-methoxy-piperidine-1-carboxylic acid (4-methoxy-7-phenyl-benzo[b]thiophen-2-yl)-amide and 4-hydroxymethyl-piperidine-1-carboxylic acid (4-methoxy-7-phenyl-benzo[b]thiophen-2-yl)-amide.

8. The compound of formula I in accordance with claim 1, wherein R is piperazinyl, substituted by methyl.

9. The compound of formula I in accordance with claim 8, wherein the compound is 4-methyl-piperazine-1-carboxylic acid (4-methoxy-7-phenyl-benzo[b]thiophen-2-yl)-amide.

10. The compound of formula I in accordance with claim 1, wherein R is selected from the group phenyl, phenyl substituted by halogen, pyridin 3- or 4-yl and pyridin 3- or 4-yl substituted by lower alkyl.

11. The compound of formula I in accordance with claim 10, wherein the compound is selected from the group consisting of N-(4-methoxy-7-phenyl-benzo[b]thiophen-2-yl)-6-methyl-nicotinamide, N-(4-methoxy-7-phenyl-benzo[b]thiophen-2-yl)-2-methyl-isonicotinamide and 4-fluoro-N-(4-methoxy-7-phenyl-benzo[b]thiophen-2-yl)-benzamide.

12. A process for preparing a compound of formula IA comprising
  a) reacting a compound of formula

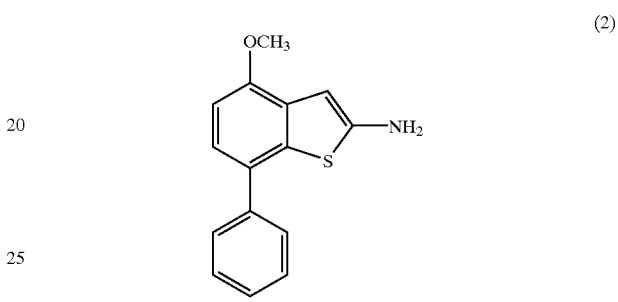

(2)

with a compound of formula

RC(O)Cl  (3)

forming a compound of formula

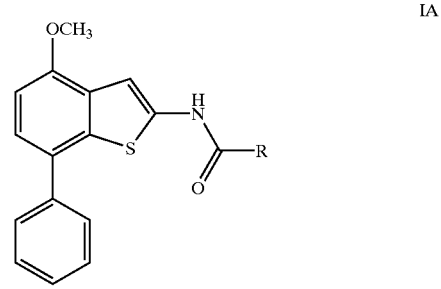

IA wherein R is phenyl, phenyl substituted by halogen, pyridin 3-or 4-yl, or pyridin 3-or 4-yl substituted by lower alkyl.

13. A process for preparing a compound of formula IB comprising
  a) reacting a compound of formula

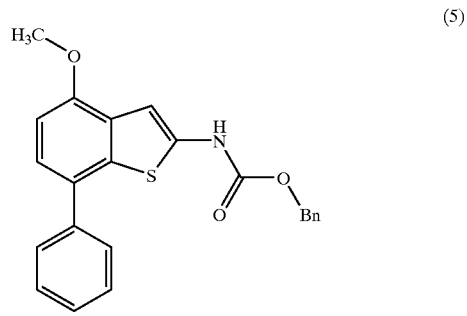

(5)

with a compound of formula $HNR^1R^2$ forming a compound of formula

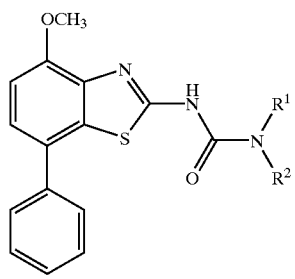

IB wherein $R^1$ and $R^2$, together with the N atom to which they are attached, form heterocyclic rings, selected from the group consisting of morpholinyl, thiomorpholinyl, piperidinyl and piperazinyl, said heterocylic rings being unsubstituted or substituted by —$(CH_2)_n$-hydroxy, lower alkyl or lower alkoxy.

14. A pharmaceutical composition comprising a therapeutically effective amount of a compound of formula I according to claim 1, or a pharmaceutically acceptable salt thereof and a pharmaceutically inert carrier.

15. A method for the treatment of Parkinson's disease comprising administering a therapeutically effective amount of a compound of formula I, or a pharmaceutically acceptable salt thereof to a person in need of such treatment.

16. A method for the treatment of ischemia comprising administering a therapeutically effective amount of a compound of formula I, or a pharmaceutically acceptable salt thereof to a person in peed of such treatment.

* * * * *

UNITED STATES PATENT AND TRADEMARK OFFICE
CERTIFICATE OF CORRECTION

PATENT NO. : 6,730,670 B2
DATED : May 4, 2004
INVENTOR(S) : Alexander Alanine and Alexander Flohr It is certified that error appears in the above-identified patent and that said Letters Patent is hereby corrected as shown below:

Column 18,
Line 16, "thereof to a person in peed of such treatment." should read -- thereof to a person in need of such treatment. --.

Signed and Sealed this

Thirteenth Day of July, 2004

JON W. DUDAS
*Acting Director of the United States Patent and Trademark Office*